United States Patent [19]

Wendel et al.

[11] Patent Number: 5,262,154

[45] Date of Patent: Nov. 16, 1993

[54] SHAVING PREPARATION

[75] Inventors: Otto W. Wendel; Pauley Chang, both of Houston, Tex.

[73] Assignee: TRP, Inc., Houston, Tex.

[21] Appl. No.: 569,653

[22] Filed: Aug. 20, 1990

[51] Int. Cl.$^5$ ............................................. A61K 7/15
[52] U.S. Cl. ......................................... 424/73; 424/47; 514/938; 514/944; 252/351
[58] Field of Search .................... 424/73, 47; 514/938, 514/944; 252/351

[56] References Cited

U.S. PATENT DOCUMENTS

| | | | |
|---|---|---|---|
| 4,822,601 | 4/1989 | Goode | 424/69 |
| 4,876,083 | 10/1989 | Grolliner | 424/73 |
| 4,963,351 | 10/1990 | Weston | 424/73 |
| 4,963,352 | 10/1990 | Roberts | 424/47 |
| 4,999,183 | 3/1991 | Mackles | 424/78 |
| 5,009,880 | 4/1991 | Grollier | 424/70 |

FOREIGN PATENT DOCUMENTS 0024161  5/1980  European Pat. Off. .
024161   2/1981  European Pat. Off. .

OTHER PUBLICATIONS

UCARE Polymers: Conditioners for all Conditions, Amerchol Corporation, 1990, 10 Pages.
Cosmetics & Toiletries, vol. 100, Nov. 85, pp. 83–89.
Balsam and Sagarin. Cosmetic: Science & Technology, vol. 2, 1972, pp. 13–36.

*Primary Examiner*—Thurman K. Page
*Assistant Examiner*—Raj Bawa
*Attorney, Agent, or Firm*—Fulbright & Jaworski

[57] ABSTRACT

A shaving preparation for curly haired men UCARE Polymer SR-10, water, Estalan 430 and Shebu W/S and methods of preparing aerosol, brushless shaving cream and gel formulations of the preparation. Each of the methods includes suspending and hydrating UCARE Polymer SR-10 in water, heating the suspension, adding the Estalan and Shebu W/S and cooling the preparation.

30 Claims, No Drawings

SHAVING PREPARATION

BACKGROUND OF THE INVENTION

This invention generally relates to the field of shaving preparations, and more particularly, to a shaving preparation for black men and other curly haired men.

Pseudofolliculitis barbae or ingrown hairs is frequently a problem for black men and other men with curly hair. The stiff hair tips penetrate the skin before leaving the follicle or they leave the follicle, curl and reenter the skin, producing a chronic low-grade irritation without significant infection. The irritation usually takes the form of small bumps or pustules that are a reaction to the foreign-body. The only consistently effective treatment for the condition has been to have the man grow a beard. Special razors have been used with varying results. Depilatories such as thioglycolate have been used but are often irritating to the skin. Topical creams and lotions containing retionic acid or benzoyl peroxide are some times effective in mild or moderate cases but they too may be irritating.

Conventional aerosol shaving creams do not sufficiently relax or straighten the hair for the razor to remove it at the skin's surface. Other conventional shaving preparations involve multiple step processes with creams or lotions that must be applied several hours to a full day in advance of shaving. Consequently, such preparations are inconvenient to use.

SUMMARY OF THE INVENTION

It, therefore, is an object of the invention to provide a shaving preparation that reduces the irritation associated with minor to moderate pseudofolliculitis barbae.

Another object of the invention is to provide a shaving preparation that can be applied for about one minute prior to shaving to relax or straighten the facial hair in preparation for shaving.

Still another object of the invention is to provide a shaving preparation that can be used in aerosol form.

Yet still another object of the invention is to provide a shaving preparation that forms a matrix of Polymer fibers which create a bed or platform between the facial hair and the skin surface.

Therefore, in accordance with one aspect of the present invention there is provided an improved shaving preparation which includes deionized, reverse osmosis or distilled water, UCARE Polymer SR-10, Estalan 430 and Shebu W/S.

In accordance with another aspect of the present invention there are provided methods of preparing an improved shaving preparation. The preparation methods include both single and multiple phase methods. Each method involves dispersing the UCARE Polymer SR-10 into the water at ambient temperatures with high speed agitation; heating the colloidal suspension; adding the other phases or ingredients, including but not limited to Estalan 430 and Shebu W/S, after the UCARE Polymer SR-10 is completely dispersed and fully hydrated; partially cooling the combined ingredients/phases during continuous mixing; adding fragrance, if desired; and cooling the preparation to ambient temperature.

In accordance with still another aspect of the present invention there is provided a method of packaging an improved shaving preparation. The packaging method includes combining the concentrated form of the shaving preparation with a hydrocarbon or fluorocarbon propellant or a blend of hydrocarbon and fluorocarbon propellants and sealing the concentrate-propellant combination in a one-piece can or a double lined aerosol can with a side seam stripe seal.

Other and still further objects, features and advantages of the present invention will be apparent from the following description of a presently preferred embodiment of the invention.

DETAILED DESCRIPTION OF PREFERRED EMBODIMENT

This invention provides a novel way of reducing the irritation associated with minor to moderate pseudofolliculitis barbae. The invention is a novel shaving preparation and methods of preparing and packaging the shaving preparation.

The preparation includes deionized, reverse osmosis or distilled water and UCARE Polymer SR-10 (hereinafter referred to as "Ingredient A"), Estalan 430 (hereinafter referred to as "Ingredient B") and Shebu W/S (hereinafter referred to as "Ingredient C"). Emulsifiers, humectants, preservatives and germicidal agents, acids, bases and fragrance can be added to the preparation as non-critical ingredients. The preparation softens the skin by reacting with the sebum in the hair follicles. The polymer creates a bed or platform between the facial hair and the skin surface. Thus, the polymer holds the hair up so that it can be removed with a razor.

In the preferred embodiment, the aerosol concentrate form of the shaving preparation includes a water phase, an oil Phase and fragrance. The water phase includes deionized, reverse osmosis or distilled water and Ingredient A. The oil phase includes Ingredient B. The preparation also includes Ingredient C, which can be added either to the water or oil phase, but is most preferably added in the oil phase. Glucamate SSE-20 (hereinafter referred to as "Ingredient D"), Butylene Glycol (hereinafter referred to as "Ingredient E"), Glucam E-20 (hereinafter referred to as "Ingredient F"), Gernaben II (hereinafter referred to as "Ingredient G"), and triethanolamine (hereinafter referred to as "Ingredient H") (see Table 1) are non-critical ingredients added to the water phase. Pristerene 4911 (hereinafter referred to as "Ingredient I"), Solulan 98 (hereinafter referred to as "Ingredient J"), and Glucate SS (hereinafter referred to as "Ingredient K") (see Table 1) are non-critical ingredients added to the oil phase. Fragrance is also added to the concentrate in the preferred embodiment.

TABLE 1

| Ingredient | Trade Name | CTFA[1] Designation | CAS[2] Nomenclature |
| --- | --- | --- | --- |
| A | UCARE Polymer SR-10 | Polyquaternium-10 | Cellulose 2-hydroxyethyl 2-[2-hydroxy-3-(trimethylammonia) propoxyl]ethyl 2-hydroxy-2-(trimethylammonia) propylether chloride |
| B | Estalan 430 | Diethylene glycol dioctanoate/ diisononanoate | None assigned |

TABLE 1-continued

| Ingredient | Trade Name | CTFA[1] Designation | CAS[2] Nomenclature |
|---|---|---|---|
| C | Shebu W/S | PEG-50 Shea Butter | None assigned[3] |
| D | Glucamate SSE-20 | PEG-20 Methyl glucose sesquistearate | Poly(oxy-1, 2-ethanediyl), ζ-hydro-ω-hydroxy-ether with methyl β-D-glucopyranoside (4:1), octadecanoate (2:3) |
| E | Butylene glycol | Butylene glycol | 1, 3 Butanediol |
| F | Glucam E-20 | Methyl gluceth-20 | Poly(oxy-1, 2 ethanediyl), ζ-hydro-ω-hydroxy-ether with methyl β-D-glucopyranoside (4:1) |
| G | Germaben II | A combination of propylene glycol and diazolidinyl urea and methylparaben and propylparaben | A combination of 1, 2 propanediol and N(hydroxymethyl)-N-(1, 3-dihydroxymethyl-2, 5-dioxo-4-imidazolidinyl)-N'-(hydroxymethyl) urea and benzoic acid, 4-hydroxymethyl ester, and benzoic acid, 4-hydroxy propyl ester |
| H | Triethanolamine, 99% | Triethanolamine (TEA) | 2,2', 2"-nitriloethanol |
| I | Pristerene 4911 | Stearic acid (triple press) | n-Octadecanoic acid |
| J | Solulan 98 | A combination of polysorbate 80 and cetylacetate and acetylated lanolin alcohol | 1 hexadecanoyl acetate |
| K | Glucate SS | Methyl glucose sesquistearate | D-glucopyranoside methyl octadecanoate (2:3) |

[1]CTFA = The Cosmetic, Toiletry and Fragrance Association
[2]CAS = Chemical Abstract Service
[3]Shea butter is fat obtained from the fruit of the Karite tree, *Butyrospermum parkii*, family Sapotaceae The amounts of all ingredients in the aerosol concentrate formulation of the shaving preparation are determined on the basis of percent weight of all the ingredients ("% w/w"). In the preferred embodiment of the aerosol concentrate formulation, the Ingredient A is about 0.1 to 2.0%; Ingredient B is about 0.05 to 1.5; Ingredient C is about 0.1 to 10.0%; and water accounts for the remainder. When one or more of the non-critical water and oil phase ingredients are added, they are used at in the following amounts: Ingredient D is about 0.2 to 4.0%; Ingredient E is about 0.1 to 15.0%; Ingredient F is proportional to the amount of Ingredient D and about 0.3 to 6.6%; Ingredient G is about 0.1 to 10.0%; Ingredient H is about 0.1 to 4.0%; Ingredient J is about 0.1 to 10.0%; Ingredient K is proportional to the Ingredient J and about 0.06 to 8.0%; Ingredient I is about 3.0 to 15.0%. Fragrance may be added to the preparation in amount ranging between about 0.1 and 1.0 % w/w.

The non-critical water and oil phase ingredients can be substituted as well as eliminated. Examples of substitutions are as follows. Ingredient I can be replaced with palmitic (hexadecanoic) acid, lauric (dodecanoic) acid or myristic (tetradecanoic) acid. Potassium hydroxide or sodium hydroxide can be used in place of Ingredient H. Ethoxyol 24 or Crodesta F-160 (Table 2) can be substituted for the Ingredient D.

TABLE 2

| Trade Name | CTFA[1] Designation | CAS[2] Nomenclature |
|---|---|---|
| Ethoxyol-24 | PEG-24 hydrogenated lanolin | Hydrogenated, ethoxylated lanolin |
| Crodesta F-160 | Sucrose stearate | β-D-fructofuransyl-ζ-D-glucopyranoside monoctadecanoate |
| Crodesta F-50 | Sucrose distearate | ζ-D-Glucopyranoside, β-D-fructofuransyl, dioctadecanoate |
| Pegosperse 100 M1 | PEG-2 laurate | Dodecanoic acid, 2-(2-hydroxyethoxy)ethyl ether |
| Emsorb 2510 | Sorbitan paloitate | Monohexadecanoate sorbitan |
| Finsolv TN | C12-15 benzoate alcohols | Benzoic acid, C12-15 alkyl esters |
| Liponic EG-1 | Glycereth-26 | Poly(oxy-1, 2-ethanediyl) ζ, ζ', ζ"-1, 2, 3-propanetriyltria [ω-hydroxy |
| Glycerine | Glycerine | 1, 2, 3-Propanetriol |
| Sorbo | Sorbitol | D-glucitol |

[1]CTFA = The Cosmetic, Toiletry and Fragrance Association
[2]CAS = Chemical Abstract Service Crodesta F-50, Pegosperse 100 Ml, Emsorb 2510, or Finsolv TN (Table 2) can be substituted for the Ingredient K. Glycerine, propylene glycol, Liponic EG-1 or sorbo (Table 2) can be substituted for Ingredient E or Ingredient F. Alternative preservatives and germicidal agents also may be used. Mineral or organic acids or bases may be added to adjust the pH.

The preferred method of preparing the aerosol concentrate formulation of the shaving preparation includes separately, but simultaneously, preparing and heating the water and oil phases, adding the oil phase to the water phase during continuous agitation, partially cooling the combined phases during continuous mixing, adding fragrance, if desired, and continuously mixing until ambient temperature is reached.

EXAMPLE 1

An aerosol formulation of the shaving preparation is a concentrate composed of deionized, reverse osmosis or distilled water, Ingredient A, Ingredient D, Ingredient E, Ingredient F, Ingredient G, and Ingredient H in a water phase; Ingredient B, Ingredient C, Ingredient I, Ingredient J, and Ingredient K in an oil phase; and fragrance. These ingredients are used as follows: about 78.0 % w/w deionized, reverse osmosis or distilled water, about 0.8 % w/w Ingredient A, about 1.0 % w/w Ingredient B, about 2.0 % w/w Ingredient C, about 1.2 % w/w Ingredient D, about 5.0 % w/w Ingredient E, 2.0 % w/w Ingredient F, about 1.0 % w/w Ingredient G, about 2.0 % w/w Ingredient H, about 9.0 % w/w Ingredient I, about 1.0 % w/w Ingredient J, about 0.8 % w/w Ingredient K, and about 0.2 % w/w fragrance.

For this aerosol concentrate, the water phase was prepared in a vessel of suitable size to accommodate an entire batch of the shaving preparation. First the vessel was charged with deionized, reverse osmosis or distilled water. Ingredient A then was hydrated by dispersing Ingredient A in the water with high speed agitation (rate of about 1200 rpm) at ambient temperature to form a colloidal suspension. After dispersion and hydration was completed, the mixture was heated about 2° C per minute to about 75°–80° C. After the Ingredient A was fully hydrated (i.e., a viscous gel is formed) and the temperature of the mixture had reached at least 60° C., the balance of the water phase ingredients (e.g., Ingredient D, Ingredient E, Ingredient F, Ingredient G, and Ingredient H) were added to the mixture.

While the water phase was being prepared, the oil phase was simultaneously but separately prepared in another vessel. The oil phase ingredients were combined in the second vessel in any order. They were continuously mixed and heated about 2° C. per minute to about 75°–80° C.

When both the water and oil phases were at about 75°–80° C., the oil phase was slowly added over a period of about five minutes to the water phase with continued adequate agitation. Agitation was at speeds allowing mixing without air entrapment. After all the oil phase had been added to the water phase, the combined phases were continually mixed for at least 20–30 minutes. The combined phases then were cooled while continuously mixed. When the combined phases were about 40–45° C., the fragrance was added. Finally, the mixture was continually mixed until the mixture reached ambient temperature. The fragrance was added to the mixture in amount approximating 0.2 % w/w. The pH of the completed aerosol formulation was approximately 7.8 to 8.2, preferably 8.0.

The aerosol concentrate formulation described above can be combined with a propellant for packaging in aerosol form. The propellant cannot be a compressed gas such as nitrogen or carbon dioxide. A hydrocarbon or fluorocarbon propellant or a blend of hydrocarbons and fluorocarbon propellants are preferred. More preferred are iso-butane or any combination of iso-butane, butane and propane. The container is either a double lined can with a side seam stripe or a one-piece container. Preferably, the liner is lacquer or epoxy.

EXAMPLE 2

A combination including about 95% aerosol concentrate of Example 1 and about 5% isobutane-propane at about 46 psi was added to an aerosol can. The can was a 202×214 double lacquered or epoxy lined can with a side stream stripe. The can was piston operated. It was fitted with a SQT NS-21 valve, a 2×020 stem, 062 Body, a Buna N gasket, a 3 5/16 dip tube, a 0.090 inch shaving creme spout and a Epon TB cup with a laminated bottom. Other proportionately sized and similarly equipped cans may be used.

The aerosol formulation of the shaving Preparation is easily converted to a thick, brushless shaving cream. The brushless shaving cream is formulated by adding about 1 to 3 % w/w cetyl alcohol (1-hexadecanol), lauryl alcohol (1-dodecanol) or myristyl alcohol (1-tetradeconol) to Ingredients A, B, & C and any non-critical ingredients. The method of preparing the brushless shaving cream is the same as the method of preparation for the aerosol concentrate formulation with the alcohol being added to the oil phase of the formulation.

EXAMPLE 3

The formulation of Example 1 is converted to a thick, brushless shave cream by adding about 2.00 % w/w cetyl alcohol to the oil phase ingredients. The method of preparation of this brushless shave cream is the same as the method for the aerosol formulation in Example 1.

An alternate brushless shave cream is prepared using a four-phase formulation. Phase 1 includes deionized, reverse osmosis or distilled water and UCARE Polymer. Phase 2 includes Liponic EG-1 (hereinafter referred to as "Ingredient L"), sodium borate, potassium hydroxide pellets, 99% triethanolamine and methylparaben (hereinafter referred to as "Ingredient M") (see Table 3). Phase 3 includes Ingredient B, Ingredient I, coconut fatty acid (hereinafter referred to as "Ingredient N"), Lipolan R (hereinafter referred to as "Ingredient O"), D-C 200 Fluid (hereinafter referred to as "Ingredient P") (350 cks) and propylparaben (hereinafter referred to as "Ingredient Q") (see Table 3). Phase 4 is fragrance. Ingredient C also is added to the formulation with the Phase 2 or Phase 3 ingredients, preferably with the Phase 3 ingredients.

TABLE 3

| Ingredient | Trade Name | CTFA[1] Designation | CAS[2] Nomenclature |
|---|---|---|---|
| A | UCARE Polymer SR-10 | Polyquaternium-10 | Cellulose 2-hydroxyethyl 2-[-hydroxy-3-(trimethylammonia)propoxyl]ethyl 2-hydroxy-2-(trimethylammonia)propylether chloride |
| L | Liponic EG-1 | Glycereth-26 | Poly(oxy-1, 2-ethanadiyl) ξ, ξ', ξ''-1,2,3-propane-triyltria [ω-hydroxy] ether |
| H | Triethanolamine, 99% | Triethanolamine (TEA) | 2, 2', 2'''-nitriloethanol |
| M | Methylparaben | Methylparaben | Benzoic acid, 4-hydroxy-methyl ester |
| I | Pristerene 4911 | Stearic acid | n-Octadecanoic acid |
| C | Shebu W/S | PEG-50 Shea butter | None issued[3] |

TABLE 3-continued

| Ingredient | Trade Name | CTFA[1] Designation | CAS[2] Nomenclature |
|---|---|---|---|
| N | Coconut fatty acid | Coconut acid | Fatty acid, coco |
| O | Lipolan R | Lanolin oil | Lanolin oil |
| P | D-C 200 Fluid | Dimethicone | Dimethyl polysiloxane |
| Q | Propylparaben | Propylparaben | Benzoic acid, 4-hydroxy-propyl ester |
| B | Estalan 430 | Diethylene glycol dioctanoate/ diisononanoate | None assigned |

[1]CTFA = The Cosmetic, Toiletry and Fragrance Association
[2]CAS - Chemical Abstract Service
[3]Shea butter is fat obtained from the fruit of the Karite tree, *Butyrospermum parkii*, family Spotaceae
[4]Derived from hydrolysis of coconut oil The amounts of all ingredients in the four-phase brushless shave cream of the shaving preparation are determined on the basis of percent weight per total weight of all the ingredients ("% w/w"). The ingredients in the four-phase brushless shave cream formulation are used in the following amounts: Ingredient A is about 0.1 to 2.0%; Ingredient B is about 0.05 to 1.0%; Ingredient C is about 0.1 to 10.0%; sodium borate is about 0.3 to 1.0%; potassium hydroxide is about 0.1 to 1.0%; Ingredient H is about 0.2 to 4.0%; Ingredient I is about 1 to 20%; Ingredient L is about 0.1 to 20.0%; Ingredient M is about 0.05 to 0.3%; Ingredient N is about 0.1 to 10.0%; Ingredient 0 is about 0.3 to 1.2%; Ingredient P is about 0.1 to 2.0%; Ingredient Q is about 0.01 to 0.3%, and fragrance is about 0.1 to 1.0%. Water accounts for the remainder. Non-critical ingredients can be substituted as in the aerosol concentrate formulation. The method of preparing the four-phase brushless shaving cream formulation includes separately, but simultaneously, preparing and heating Phases 1 and 3; thereafter adding Phase 2 ingredients directly into Phase 1 during continuous mixing; then adding combined Phases 1+2 to Phase 3 while mixing with rapid agitation (at a rate of about 800 rpm); maintaining Phases 1+2+3 at 75°-80° C. for a minimum of 45 minutes; thereafter continuously mixing and partially cooling combined Phases 1+2+3 to about 40°-45° C.; adding Phase 4; and finally continuously mixing and cooling the four-phase formulation until ambient temperature is reached.

EXAMPLE 4

A four-phase brushless shaving cream formulation of the shaving preparation is a mixture of about 67.2 % w/w deionized, reverse osmosis or distilled water, about 0.8% w/w Ingredient A, about 1.0 % w/w Ingredient B, about 2.0% w/w Ingredient C, about 0.5 % w/w sodium borate, about 0.2% w/w potassium hydroxide pellets, about 0.35 % w/w 99% Ingredient H, about 18.0 % w/w Ingredient I, about 10.0% w/w Ingredient L, about 0.07 % w/w Ingredient M, about 2.0% w/w Ingredient N, about 0.5 % w/w Ingredient O, about 0.25% w/w Ingredient P, about 0.3 % w/w Ingredient Q, and about 0.1 % w/w fragrance.

The method of preparation of this four-phase formulation is as follows. The water is added to a vessel. Ingredient A is dispersed into the water and agitated at high speed (rate of about 1200 rpm) to make colloidal suspension. When Ingredient A is thoroughly dispersed and completely hydrated, agitation is reduced to a rate of mixing that avoids air entrapment. Then the Phase 2 ingredients are added directly into Phase 1. The Phase 2 ingredients are added in any order and are slowly mixed at a rate of about 300 rpm. During mixing, the combined Phase 1+2 mixture is heated to about 80° C. over a period of about 25 minutes. The Phase 3 ingredients are combined in a second vessel and mixed slowly at a rate that avoid air entrapment. The Phase 3 ingredients are heated to about 80° C. over a period of about 30 minutes. When both the Phase 1+2 mixture and Phase 3 mixture are uniform and at about 85° C., over a period of about five minutes, the combined Phases 1+2 are slowly added to Phase 3 with rapid agitation (rate of about 800 rpm). Then the combined Phases 1+2+3 are maintained at about 85° C. for about 15 minutes or longer. Thereafter they are simultaneously cooled over a period of about 60 minutes to about 35° C. and mixed at a speed adjusted to compensate for increased consistency. When the temperature of the mixture is about 35° C., Phase 4 is added to the combined Phases 1+2+3 and mixed until uniform. The shaving preparation is then continually mixed and cooled until ambient temperature is reached.

Another formulation of the shaving preparation uses a single phase formula. The single phase formula produces a shaving gel. The ingredients (Table 4) include deionized, reverse osmosis or distilled water, Ingredient A, Ingredient B, Ingredient C, Ingredient G triethanolamine lauryl sulfate (40%) (hereinafter referred to as "Ingredient R"), disodium laurethsulfosuccinate (40%), (hereinafter referred to as "Ingredient S"), and Tween 20 (hereinafter referred to as "Ingredient T"). Fragrance may also be added.

TABLE 4

| Ingredient | Trade Name | CTFA[1] Designation | CAS[2] Nomenclature |
|---|---|---|---|
| A | UCARE Polymer SR-10 | Polyquaternium-10 | Cellulose, 2-hydroxyethyl 2-[2-hydroxy-3-(trimethylammonia) propoxyl]ethyl 2-hydroxy-2-(trimethylammonia) propylether chloride |
| C | Shebu W/S | Shea butter | None assigned[3] |
| R | Triethanolamine lauryl sulfate | TEA lauryl sulfate | Triethanolamine lauryl sulfate |
| S | Schercopol LPS | Disodium laureth sulfosuccinate | Poly (oxy-1,2-ethanediyl), ζ-(3-carboxy-1-oxo-3-sulfo-propyl)-ω-dodecyloxy-disodium salt |
| T | Tween 20 | Polysorbate 20 | Sorbitan, monododecanoate, poly (oxy-1,2-ethanediyl) derivatives |

TABLE 4-continued

| Ingredient | Trade Name | CTFA[1] Designation | CAS[2] Nomenclature |
|---|---|---|---|
| G | Germaben II | Combination of propylene glycol and diazolidinyl urea and methylparaben and propylparben | A combination of 1,2 propanediol and N(hydroxymethyl-N-(1,3, dihydroxymethyl-2,5-dioxo-4-imidazolidinyl)-N'-hydroxymethyl) urea and benzoic acid, 4-hydroxymethyl ester and benzoic acid, 4-hydroxypropyl ester |
| B | Estalan 430 | Diethylene glycol dioctanoate/diisonononanoate | None issued |

[1]CTFA = The Cosmetic, Toiletry and Fragrance Association
[2]CAS = Chemical Abstract Service
[3]Shea butter is fat obtained from the fruit of the Karite tree, *Butyrospermum parkii*, family Spotaceae
[4]Polyoxyethylene derivative of fatty acid partial esters of sorbitol anhydrydes The amounts of all ingredients in the gel formulation are determined on the basis of percent weight per total weight of all the ingredients (% w/w). The ingredients in the gel formulation are used in the following amounts: Ingredient A is about 1.5 to 2.5%; Ingredient B is about 0.05 to 1.5%; Ingredient C is about 0.1 to 10.0%; Ingredient G is about 0.1 to 1.5%; Ingredient R is about 15 to 30%; Ingredient S is about 8 to 15%; Ingredient T is about 1.0 to 3.0%; and fragrance is about 0.1 to 1.0%. Water accounts for the remainder. As with the other formulations of the shaving preparations, Ingredient A, Ingredient B and Ingredient C are the critical ingredients. The non-critical ingredients in the gel formulation can be substituted. For example, alternative preservatives and germicidal agents may be used in place of the Ingredient G.

In preparing the gel formulation, Ingredient A is dispersed into water at ambient temperatures with high speed agitation (rate of about 1800 rpm) to form a colloidal suspension. The collidal suspension is continuously stirred and heated over at period of about 25 minutes to about 60° C. When the polymer is fully hydrated (i.e., a viscous gel is formed), with the exception of fragrance, the balance of the ingredients are added. The mixture is partially cooled during continuous mixing. Fragrance, if desired, is added and the gel is further cooled and mixed until ambient temperature is reached.

EXAMPLE 5

The gel formulation of the shaving preparation is a mixture composed of about 56.8 % w/w deionized, reverse osmosis or distilled water, about 2.0 % w/w Ingredient A, about 1.0 % w/w Ingredient B, about 2.0 % w/w Ingredient C, 1.0 % w/w Ingredient G, 25.0 % w/w Ingredient R (40%), 12.5% w/w Ingredient S (40%), 2.6 % w/w Ingredient T, and 0.1% w/w fragrance.

The method of preparing this shaving gel is as follows. The water is added to a vessel. Ingredient A is then hydrated by dispersing the Ingredient A in the water with high speed agitation (rate of about 1200 rpm) at ambient temperature to form a colloidal suspension. After dispersion is completed, the mixture is slowly heated to about 75°-80° C. over a period of about 25 minutes. When the Ingredient A is fully hydrated and the temperature of the mixture has reached at least 60° C., the following ingredients are added sequentially: Ingredient R, Ingredient S, Ingredient T and Ingredient G. The mixture is thoroughly mixed between each addition of ingredients. After all the ingredients, except fragrance, have been added, the mixture is cooled to about 35° C. during constant mixing at a rate of about 300 rpm. Fragrance then is added and the mixture is continuously mixed and cooled until ambient temperature is reached.

One skilled in the art will readily appreciate that the present invention is well adapted to carry out the objects and obtain the ends and advantages mentioned, as well as others inherent therein. While the presently preferred embodiments of the invention have been described for the purpose of disclosure, numerous changes in the details of the formulations and their methods of synthesis may be made without departing from the spirit of the present invention and scope of the appended claims. It should be understood, however, that there is no intention to limit the invention to the specific formulations or methods disclosed, but on the contrary, the intention is to cover all modifications, alternative formulations, methods and equivalents falling within the spirit of the present invention and the scope of the appended claims.

What is claimed is:

1. A shaving preparation consisting essentially of:
   a mixture of water, polyquaternium-10 diethylene glycol dioctanoate/diisononanoate and PEG-50 shea butter wherein said polyquaternium-10 is fully hydrated in said water before combination with said diethylene glycol dioctanoate/diisononanoate and said PEG-50 shea butter and said polyquaternium-10 has a viscosity specification of 8,000–12,000 cps at 25° C.

2. The shaving preparation of claim 1 wherein said water comprises deionized, reverse osmosis or distilled water.

3. The shaving preparation of claim 1 wherein aid polyquaternium-10 is about 0.1 to 2.0% by weight, said diethylene glycol dioctanoate/diisononanoate is about 0.05 to 1.5% by weight and said PEG-50 shea butter is about 0.1 to 10.0% by weight.

4. A shaving preparation consisting essentially of:
   a concentrate including a water phase and an oil phase;
   said water phase comprising water and polyquaternium-10 wherein said polyquaternium-10 is fully hydrated in said water and said polyquaternium-10 has a viscosity specification of 8,000–12,000 cps at 25° C.;
   said oil phase comprising a mixture of diethylene glycol dioctanoate/diisononanoate and PEG-50 shea butter; and
   said oil phase is added to said water phase.

5. The shaving preparation of claim 4 wherein said water comprises deionized, reverse osmosis or distilled water.

6. The shaving preparation of claim 4 further including the addition of fragrance after said oil phase is added to said water phase.

7. A shaving preparation consisting essentially of:
a concentrate including a water phase and an oil phase;
said water phase comprising water, polyquaternium-10 and PEG-50 shea butter wherein said polyquaternium-10 is fully hydrated in said water before the addition of said PEG-50 shea butter and said polyquaternium-10 has a viscosity specification of 8,000–12,000 cps at 25° C.;
said oil phase comprising diethylene glycol dioctanoate/diisononanoate; and
said oil phase is added to said water phase.

8. The shaving preparation of claim 7 wherein said water comprises deionized, reverse osmosis or distilled water.

9. The shaving preparation of claim 7 further including the addition of fragrance after said oil phase is added to said water phase.

10. A shaving preparation consisting essentially of:
a water phase, said water phase including water and polyquaternium-10 wherein said polyquaternium-10 is fully hydrated in said water and said polyquaternium-10 has a viscosity specification of 8,000–12,000 cps at 25° C.; and
an oil phase added to said water phase, said oil phase including diethylene glycol dioctanoate/diisononanoate and PEG-50 shea butter.

11. The shaving preparation of claim 10 wherein said water comprises deionized, reverse osmosis or distilled water.

12. The shaving preparation of claim 10 further including the addition of fragrance after said oil phase is added to said water phase.

13. A shaving preparation consisting essentially of:
a water phase, said water phase including water, polyquaternium-10 and PEG-50 shea butter wherein said polyquaternium-10 is fully hydrated in said water before the addition of said PEG-50 shea butter and said polyquaternium-10 has a viscosity specification of 8,000–12,000 cps at 25° C.; and
an oil phase added to said water phase, said oil phase including diethylene glycol dioctanoate/diisononanoate.

14. The shaving preparation of claim 13 wherein said water comprises deionized, reverse osmosis or distilled water.

15. The shaving preparation of claim 13 further including the addition of fragrance after said oil phase is added to said water phase.

16. A brushless shaving cream preparation consisting essentially of:
a mixture including a water phase and an oil phase;
said water phase comprising water and polyquaternium-10 wherein said polyquaternium-10 is fully hydrated said water and said polyquaternium-10 has a viscosity specification of 8,000–12,000 cps at 25° C.;
said oil phase comprising a mixture of diethylene glycol dioctanoate/diisononanoate, PEG-50 shea butter and alcohol; and
said oil phase is added to said water phase.

17. The shaving preparation of claim 16 wherein said alcohol comprises cetyl alcohol, lauryl alcohol, myristyl alcohol or a combination thereof.

18. A brushless shaving cream preparation consisting essentially of:
a mixture including a water phase and an oil phase;
said water phase comprising water, polyquaternium-10 and PEG-50 shea butter wherein said polyquaternium-10 is fully hydrated in said water before the addition of said PEG-50 shea butter and said polyquaternium-10 has a viscosity specification of 8,000–12,000 cps at 25° C; and
said oil phase comprising diethylene glycol dioctanoate/diisononanoate and cetyl alcohol; and
said oil phase is added to said water phase.

19. The shaving preparation of claim 18 wherein said alcohol comprises cetyl alcohol, lauryl alcohol, myristyl alcohol or a combination thereof.

20. A brushless shaving cream preparation consisting essentially of:
a water-phase, said water phase including water and polyquaternium-10 wherein said polyquaternium-10 is fully hydrated said water and said polyquaternium-10 has a viscosity specification of 8,000–12,000 cps at 25° C.; and
an oil phase added to said water phase, said oil phase including diethylene glycol dioctanoate/diisononanoate, PEG-50 shea butter and cetyl alcohol.

21. The shaving preparation of claim 20 wherein said alcohol comprises cetyl alcohol, lauryl alcohol, myristyl alcohol or a combination thereof.

22. A brushless shaving cream preparation consisting essentially of:
a water phase, said water phase including water, polyquaternium-10 and PEG-50 shea butter wherein said polyquaternium-10 is fully hydrated in said water before the addition of said PEG-50 shea butter and said polyquaternium-10 has a viscosity specification of 8,000–12,000 cps at 25° C.; and
an oil phase added to said water phase, said oil phase including diethylene glycol dioctanoate/diisononanoate and cetyl alcohol.

23. The shaving preparation of claim 22 wherein said alcohol comprises cetyl alcohol, lauryl alcohol, myristyl alcohol or a combination thereof.

24. A brushless shaving cream preparation consisting essentially of:
a mixture including four phases;
said first phase comprising water and polyquaternium-10 wherein said polyquaternium-10 is fully hydrated said water and said polyquaternium-10 has a viscosity specification of 8,000–12,000 cps at 25° C.;
said second phase comprising glycereth-26, sodium borate, potassium hydroxide, triethanolamine and methylparaben;
said third phase comprising diethylene glycol dioctanoate/diisononanoate, PEG-50 shea butter, stearic acid, coconut acid, lanolin oil, dimethicone and propylparaben; and
said fourth phase comprising fragrance.

25. The shaving cream of claim 24 wherein said polyquaternium-10 is about 0.1 to 2.0% by weight, said diethylene glycol dioctanoate/diisononanoate is about 0.05 to 1.5% by weight, said PEG-50 shea butter is about 0.1 to 10.0% by weight, said sodium borate is about 0.3 to 1.0% by weight, said potassium hydroxide is about 0.1 to 0.4% by weight, said triethanolamine is about 0.2 to 4.0% by weight, said stearic acid is about 1.0 to 20.0% by weight, said glycereth-26 is about 0.1 to 20.0% by weight, said methylparaben is about 0.03 to 0.1% by weight, said coconut acid is about 0.1% to 10.0% be weight, said lanolin oil is 0.3 to 1.2% by weight, said dimethicone is about 0.1 to 1.0% by weight, said propylparaben is about 0.01 to 1.0% by weight, and said fragrance is about 0.1 to 1.0% of the total weight of said mixture.

26. The shaving cream preparation of claim 25 wherein said water is about 67.2%, said polyquaternium-10 is about 0.8%, said diethylene glycol dioctanoate/diisononanoate is about 0.05 to 1.5%; said PEG-50 shea butter is about 2.0%, said sodium borate is about 0.5%, said potassium hydroxide is about 0.2%, said triethanolamine is about 0.35%, said stearic acid is about 18.0%, said glycereth-26 is about 10.0%, said methylparaben is about 0.07%, said coconut acid is about 2.0%, said lanolin oil is about 0.5%, said dimethicone is about 0.25%, said propylparaben is about 0.3%, and said fragrance is about 0.1% of the total weight of said mixture.

27. A shaving gel preparation consisting essentially of:
a mixture including water, polyquaternium-10, diethylene glycol dioctanoate/diisononanoate, PEG-50 shea butter, germaben II comprising a combination of propylene glycol, diazolidinyl urea, methylparaben and propylparaben, triethanolamine lauryl sulfate, disodium laureth sulfosuccinate, and polysorbate 20, wherein said polyquaternium-10 is fully hydrated in said water before the addition of the remainder of the ingredients and said polyquaternium-10 has a viscosity specification of 8,000–12,000 cps at 25° C.

28. The shaving gel preparation of claim 27 further including the addition of fragrance.

29. The shaving gel preparation of claim 28 wherein said polyquaternium-10 is about 1.5 to 2.5% by weight, said diethylene glycol dioctanoate/diisononanoate is about 0.5 to 1.5% by weight, said PEG-50 shea butter is about 0.1 to 10.0% by weight, said germaben II comprising a combination of propylene glycol, diazolidinyl urea, methylparaben and propylparaben is about 0.1 to 10.0% by weight, said triethanolamine lauryl sulfate is about 15 to 30% by weight, said disodium laureth sulfosuccinate is about 8 to 15% by weight, said polysorbate 20 is about 1 to about 3% by weight, and said fragrance is about 0.1 to 1.0% of the total weight of said mixture.

30. The shaving gel preparation of claim 29 wherein said water is about 56.8%, said polyquaternium-10 is about 2.0%, said diethylene glycol dioctanoate-diisononanoate is about 1.0%, said germaben II comprising a combination of propylene glycol, diazolidinyl urea, methylparaben and propylparaben is about 1.0%, said triethanolamine lauryl sulfate is about 25.0%, said disodium laureth sulfosuccinate is about 12.5%, said weight of said mixture.

* * * * *